United States Patent [19]

Nakamura et al.

[11] 4,386,017
[45] May 31, 1983

[54] PREPARATION OF IMPROVED CATALYST COMPOSITION

[75] Inventors: Tadasi Nakamura; Minoru Osugi; Yoriko Obata; Shuji Ebata, all of Niigata, Japan

[73] Assignee: Mitsubishi Gas Chemical Company, Tokyo, Japan

[21] Appl. No.: 205,594

[22] Filed: Nov. 10, 1980

[30] Foreign Application Priority Data

Nov. 12, 1979 [JP] Japan .............................. 54-146325

[51] Int. Cl.$^3$ ................... B01J 23/08; B01J 21/02; B01J 27/24
[52] U.S. Cl. ................................ 252/463; 252/432; 252/438
[58] Field of Search ..................... 252/432, 438, 463

[56] References Cited

U.S. PATENT DOCUMENTS

| | | | |
|---|---|---|---|
| 1,956,585 | 5/1934 | Oglesby et al. | 252/463 |
| 3,971,735 | 7/1976 | Asano et al. | 252/432 |
| 4,129,523 | 12/1978 | Snowden | 252/463 X |

FOREIGN PATENT DOCUMENTS

| | | | |
|---|---|---|---|
| 2026165 | 5/1970 | Fed. Rep. of Germany | 252/463 |
| 2026182 | 12/1971 | Fed. Rep. of Germany | 252/463 |
| 2302658 | 8/1973 | Fed. Rep. of Germany | 252/463 |
| 1542044 | 6/1979 | Fed. Rep. of Germany | 252/463 |
| 1159035 | 7/1969 | United Kingdom | |
| 1286970 | 8/1972 | United Kingdom | |
| 1296212 | 11/1972 | United Kingdom | 252/463 |
| 1405012 | 9/1975 | United Kingdom | 252/463 |
| 2047556 | 12/1980 | United Kingdom | 252/463 |
| 399097 | 1/1974 | U.S.S.R. | 252/463 |
| 403427 | 3/1974 | U.S.S.R. | 252/463 |
| 709163 | 1/1980 | U.S.S.R. | 252/463 |

*Primary Examiner*—Delbert E. Gantz
*Assistant Examiner*—William G. Wright
*Attorney, Agent, or Firm*—Wenderoth, Lind & Ponack

[57] ABSTRACT

A process for preparing a catalyst composition comprising copper oxide, zinc oxide and aluminum oxide as essential ingredients and optionally containing boron oxide, which comprises (a) a step of precipitating from an aqueous solution of a water-soluble copper salt optionally containing a water-soluble boron compound the copper component, together with the boron component if it is present, using an alkaline substance selected from alkali carbonates and alkali bicarbonates as a precipitant;

(b) a step of blowing carbon dioxide gas into an aqueous dispersion of a zinc compound selected from zinc oxide and zinc hydroxide optionally containing a water-soluble boron compound to convert the zinc compound to basic zinc carbonate and simultaneously precipitate the boron component if it is present; and (c) a step of calcining a mixture of the solid products obtained in steps (a) and (b) in the presence of an alumina precursor compound.

The resulting catalyst is useful for synthesizing methanol from a gaseous mixture of carbon monoxide and/or carbon dioxide and hydrogen.

17 Claims, No Drawings

PREPARATION OF IMPROVED CATALYST COMPOSITION

This invention relates to a catalyst composition having improved properties. More specifically, the invention relates to a method for preparing a catalyst composition stably by a simplified process at a reduced cost while maintaining a good reproducibility of the quality of the catalyst; the catalyst composition prepared by this method; and to the use of the catalyst composition. The catalyst shows high activity at relatively low temperatures and pressures, has high mechanical strength properties such as abrasion resistance and compressive strength, and is suitable especially for use in synthesizing methanol from a gaseous mixture of carbon monoxide and/or carbon dioxide and hydrogen.

Copper-zinc type or copper-zinc-chromium type catalysts have generally been used for synthesizing methanol by a vapor-phase method from carbon monoxide and/or carbon dioxide and hydrogen. Synthesis of methanol with these catalysts, however, generally requires high temperatures of more than 280° C. and high pressures of more than 150 atmospheres and the conversion to methanol is low. Moreover, these catalysts have the defect of poor heat resistance and durability and cannot withstand long-term use.

In recent years, to save energy such as for pressurization, it has increasingly been desired to develop a technique of preparing methanol under relatively low pressures of from 50 to 150 atmospheres, and catalysts with higher activity have been required. In an attempt to meet this desire, there have been proposed methanol-synthesizing catalysts comprising oxides of copper, zinc and aluminum (see British Pat. Nos. 1,159,035 and 1,286,970; these catalysts are referred to hereinbelow as "Cu-Zn-Al three-component catalyst") and methanol-synthesizing catalysts comprising oxides of copper, zinc, aluminum and boron (see U.S. Pat. No. 3,971,735; the catalysts are referred to hereinbelow as "Cu-Zn-Al-B four-component catalysts"). All of the proposed catalysts, however, are produced by a co-precipitation method and their properties such as catalytic activity and mechanical strength are not entirely satisfactory in commercial practice. It is desired therefore to improve these catalysts further.

It is a primary object of this invention to provide a catalyst composition having markedly improved catalytic activity and superior mechanical strength and being especially suitable as a catalyst for synthesis of methanol.

Another object of this invention is to provide a novel process for preparing with good reproducibility a Cu-Zn-Al three-component or Cu-Zn-Al-B four-component catalyst composition which has excellent catalytic activity at relatively low temperatures and pressures, a low abrasion rate and high compressive strength and excellent moldability.

Still another object of this invention is to provide a process for producing a catalyst composition having such excellent performance by simplified process steps at a reduced cost of production.

A further object of this invention is to provide a catalyst composition produced by the aforesaid novel process.

A yet further object of this invention is to provide a process for synthesizing methanol using the aforesaid catalyst composition.

Other objects and advantages of this invention will become apparent from the following description.

It has now been found in accordance with this invention that the above objects of this invention are attained by separately precipitating copper and zinc components using specified precipitants therefor, instead of co-precipitating them, in the preparation of the aforesaid Cu-Zn-Al three-component or Cu-Zn-Al-B four-component catalyst. This discovery has led to the present invention.

The present invention in a major aspect provides a process for preparing a catalyst composition consisting essentially of copper, zinc and aluminum oxides and if desired, containing boron oxide, which comprises (a) a step of precipitating, from an aqueous solution of a water-soluble copper salt optionally containing a water-soluble boron compound, the copper component, together with the boron component if it is present, using an alkaline substance selected from alkali carbonates and alkali bicarbonates as a precipitant;

(b) a step of blowing carbon dioxide gas into an aqueous dispersion of a zinc compound selected from zinc oxide and zinc hydroxide optionally containing a water-soluble boron compound to convert the zinc compound to basic zinc carbonate and to simultaneously precipitate the boron component if it is present; and (c) a step of calcining a mixture of the solid products obtained in steps (a) and (b) in the presence of an alumina precursor compound.

The process of this invention is characterized by the fact that the copper component is formed by precipitating from an aqueous solution of a water-soluble copper salt, and the zinc component is formed by blowing carbon dioxide gas into an aqueous dispersion of an insoluble zinc compound selected from zinc oxide and zinc hydroxide to convert it to basic zinc carbonate, instead of co-precipitating them from their soluble salts.

The water-soluble copper salt used in step (a) may include any water-soluble salts of copper that have been conventionally used in the production of Cu-Zn-Al three-component and Cu-Zn-Al-B four-component catalysts. Specific examples are cupric nitrate, cupric acetate and cupric oxalate. Those which do not contain elements acting as catalyst poisons, such as halogen or sulfur, are preferred. Cupric nitrate is especially preferred.

The water-soluble copper salt is subjected to a precipitation treatment with an alkaline precipitant from its solution in an aqueous medium such as water (deionized water). The concentration of the water-soluble copper salt in the aqueous solution is not critical and may be varied widely according to the type of the copper salt used, etc. Advantageously, the concentration is generally from 0.1 to 2.0 moles/liter (much lower than the solubility), preferably 0.25 to 1.0 mole/liter.

The alkaline precipitant for precipitating the copper component as an insoluble solid from the aqueous solution of the water-soluble copper salt is an alkali carbonate or an alkali bicarbonate.

The alkali carbonate and alkali bicarbonate used in the process of this invention include water-soluble carbonates and bicarbonates of alkali metals, and ammonium carbonate and ammonium bicarbonate. Specific examples of the water-soluble alkali metal carbonates and bicarbonates include sodium carbonate, potassium carbonate, lithium carbonate, sodium bicarbonate, and potassium bicarbonate. Of these, ammonium carbonate and ammonium bicarbonate are especially preferred.

If, for example, the copper salt is cupric nitrate and the precipitant is ammonium bicarbonate, the precipitate-forming reaction in step (a) in the process of this invention proceeds in accordance with the following reaction equation.

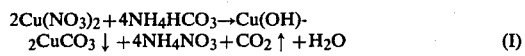

$$2Cu(NO_3)_2 + 4NH_4HCO_3 \rightarrow Cu(OH)_2CuCO_3 \downarrow + 4NH_4NO_3 + CO_2 \uparrow + H_2O \qquad (I)$$

As a result, basic copper carbonate [$Cu(OH)_2CuCO_3$] is precipitated as a water-insoluble solid. The alkali carbonate or alkali bicarbonate used in the precipitate-forming reaction may be used as such or as an aqueous solution. In either case, it is advantageous that the amount of the alkali carbonate or alkali bicarbonate used is generally at least 0.8 equivalent, preferably 1.0 to 2.0 equivalents, more preferably 1.0 to 1.3 equivalents, per equivalent of the copper salt to be precipitated.

The temperature of the precipitate-forming reaction is not critical and can be varied over a wide range. The precipitate-forming reaction can generally be performed at ambient temperature or, if desired, with heating at a temperature of up to about 60° C., preferably up to about 50° C. Under these conditions, the precipitate-forming reaction proceeds very smoothly, and can usually be completed nearly quantitatively within about 15 minutes. The resulting slurry containing the insoluble copper component dispersed therein can be subjected without after-treatment to the subsequent step.

In step (b) of the process of this invention, the zinc component, i.e., basic zinc carbonate, is formed by blowing carbon dioxide gas into an aqueous solution of a water-insoluble zinc compound selected from zinc oxide and zinc hydroxide. Zinc oxide and zinc hydroxide can equally be used as the starting zinc compound in step (b). Zinc oxide, however, can be obtained at a lower cost, and is therefore industrially advantageous.

The zinc compound may be added as such to the slurry of copper. Preferably, it is added in the form of an aqueous dispersion of the zinc compound prepared by dispersing the zinc compound in finely divided form to an aqueous medium such as water (deionized water). The aqueous dispersion may be prepared by dispersing commercial zinc oxide or zinc hydroxide powder in water with stirring using a propeller-type stirrer or a reciprocating-type stirrer. The zinc oxide or zinc hydroxide to be dispersed in the aqueous medium is desirably as fine as possible, and may have an average particle diameter of generally not more than 100 microns, preferably not more than 50 microns. Zinc oxide and zinc hydroxide in such a finely divided form are commercially available, and, for example, zinc oxide stipulated in JIS (Japanese Industrial Standards) K-1410 can be used.

The concentration of the zinc compound in the aqueous dispersion is not strictly limited, but advantageously, it is generally 5 to 30% by weight, preferably 7 to 20% by weight, based on the weight of the aqueous dispersion.

The aqueous dispersion prepared as above is added to the aforesaid copper slurry, and then carbon dioxide gas is blown into the mixture, whereby zinc oxide or zinc hydroxide is converted to basic zinc carbonate.

The basic zinc carbonate, as referred to herein, is expressed by the formula $2ZnCO_3 \cdot 3Zn(OH)_2 \cdot H_2O$.

Carbon dioxide gas is preferably free from elements which may become a catalyst poison, such as halogen or sulfur. It is generally preferred to gasify liquefied carbon dioxide and to blow the resulting carbon dioxide gas into the aqueous dispersion of the zinc compound. The amount of the carbon dioxide gas blown is not critical and can be varied widely. The suitable amount of carbon dioxide is such that the mole ratio of carbon dioxide to the zinc compound in the aqueous dispersion is generally from 0.3 to 2.0, preferably from 0.4 to 1.0.

It is sufficient that the temperature of the aqueous dispersion at the time of blowing carbon dioxide gas into it is room temperature. If required, however, it may be heated to a temperature of about up to about 100° C., preferably up to about 80° C. The time required for blowing carbon dioxide gas, i.e. the reaction time, is not critical, and can be varied depending upon the temperature of the aqueous dispersion, the degree of stirring, the rate of blowing carbon dioxide gas, the dispersibility of the carbon dioxide gas, etc. At room temperature, the reaction is usually completed within about 3 hours. Accordingly, the rate of blowing carbon dioxide gas is not critical, but preferably, the required amount of carbon dioxide is introduced at room temperature over the course of 2 to 2.5 hours.

The reaction of the zinc compound (e.g., zinc oxide) with carbon dioxide gas in the presence of water proceeds smoothly according to the following reaction scheme.

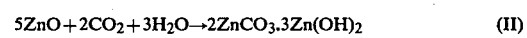

$$5ZnO + 2CO_2 + 3H_2O \rightarrow 2ZnCO_3 \cdot 3Zn(OH)_2 \qquad (II)$$

As a result, basic zinc carbonate forms in the form of an aqueous slurry.

The resulting slurry may be subjected without treatment to the subsequent step. Advantageously, however, the slurry is aged by maintaining it at a temperature of preferably about 60° to about 100° C., especially preferably about 70° to about 90° C., for at least 5 minutes, usually for 10 to 60 minutes (advantageously while continuing the blowing of carbon dioxide gas into the slurry) before it is treated in the subsequent step.

When it is desired to produce a Cu-Zn-Al-B four-component catalyst in this invention, a water-soluble compound of boron may be dissolved in one or both of the aqueous solution of the water-soluble copper salt in step (a) and the aqueous dispersion of the water-insoluble zinc compound in step (b) before the reaction in step (a) and/or (b).

The water-soluble compound of boron used in this invention may be any water-soluble boron compounds which have been conventionally used in the preparation of Cu-Zn-Al-B four-component catalysts. Examples include boric acid, borax, ammonium borate, sodium metaborate and potassium borate. Of course, these water-soluble boron compounds should desirably be free from elements which act as catalyst poisons, such as halogen and sulfur. Particularly preferred water-soluble boron compounds are boric acid and borax.

The amount of the water-soluble boron compound to be dissolved can be varied depending upon the content of the boron component required in the four-component catalyst. As required, the water-soluble boron compound can be added to the aqueous solution of the copper salt and/or the aqueous dispersion of the zinc compound in such an amount that the B/Zn atomic ratio is generally from 0.1 to 1.5.

When the water-soluble boron compound is used, therefore, there is no need to change the amounts of the precipitant and carbon dioxide gas used, and steps (a) and (b) can be carried out under substantially the same conditions as those employed in the absence of the water-soluble boron compound.

According to the present invention, the reactions for forming the precipitate of the copper compound and the basic zinc carbonate in steps (a) and (b) respectively can be carried out continuously in a single reaction vessel in this or reverse sequence. Or these two steps may be performed as independent steps in separate reaction vessels.

When the reactions in steps (a) and (b) are to be performed successively in a single reactor, steps (a) and (b) can be performed in the following sequences.

In the following description, "solution A" means an aqueous solution of a water-soluble copper salt optionally containing a water-soluble boron compound; "agent B" refers to an alkali carbonate or an alkali bicarbonate or an aqueous solution thereof; and "dispersion C" means an aqueous dispersion of zinc oxide or zinc hydroxide optionally containing a water-soluble boron compound.

(i) Agent B is added to solution A, or vice versa. They are reacted under the aforesaid conditions to precipitate the copper component fully. Dispersion C or a fine powder of zinc oxide or zinc hydroxide is added to the resulting aqueous slurry of the copper component, and they are fully mixed with stirring. Then, carbon dioxide is blown into the mixture to convert the zinc compound to basic zinc carbonate, and if desired, the product is aged.

(ii) Carbon dioxide gas is blown into dispersion C to convert the zinc compound fully to basic zinc carbonate. Then, to the resulting aqueous slurry of the basic zinc carbonate are added successively solution A or the water-soluble zinc salt itself and agent B in this or reverse sequence. They are reacted under the aforesaid conditions to precipitate the copper component. Then, if desired, the product is aged.

(iii) The water-soluble copper salt and zinc oxide or zinc hydroxide powder are both dissolved or dispersed in an aqueous medium to prepare an aqueous liquid in which the zinc compound powder is dispersed in an aqueous solution of the water-soluble copper salt. Agent B is added to the aqueous liquid to precipitate the copper component fully. Then, carbon dioxide gas is blown into the liquid to convert the zinc compound to basic zinc carbonate. Then, if desired, the product is aged.

It has been found that if aging is to be carried out, it is preferable for good physical properties of the final catalyst to perform the precipitate-forming reaction at a relatively low temperature ranging from ambient temperature to 60° C., preferably at ambient temperature, and then to perform the aging by maintaining a relatively high temperature in the range of from about 60° to about 100° C., preferably from about 70° to about 90° C.

As an alternative method, steps (a) and (b) of the process of this invention may be effected in separate reaction vessels. In this embodiment, no particular restriction is imposed on the sequence of charging solution A and agent B into the reactor in step (a), and they may be charged in any sequence. Aging may be carried out under the aforesaid conditions after the precipitate-forming reaction in each of the steps. Advantageously, however, the slurries formed by the steps are mixed upon completion of the reactions in these steps, and then the mixture is aged as required.

In the process of this invention, the solid product of the precipitate-forming reaction of step (a) and basic zinc carbonate obtained by the reaction of step (b) are mixed with stirring, preferably in the slurried state, as stated hereinabove. Desirably, this mixing is carried out as intimately as possible, and for example, it is convenient to carry out the mixing in a stirrer having a baffler plate.

The resulting slurry mixture is, if desired, aged as mentioned earlier, and then, the reaction solvent is separated from it by ordinary means such as filtration. The separated product is washed thoroughly to remove the remaining precipitant, and then calcined in the presence of an alumina precursor compound.

In the present application, the "alumina precursor compound" denotes a compound which gives alumina upon thermal decomposition under the calcination conditions to be described hereinbelow and which after decomposition does not leave a substance poisonous to the catalyst of this invention, such as sulfur or halogen. The alumina precursor compound includes a so-called alumina sol, or aluminum hydroxide or the like which is obtained by precipitation from an aqueous solution of a water-soluble aluminum compound (e.g., sodium aluminate, aluminum acetate or aluminum nitrate) by precipitating means such as hydrolysis or treatment with a precipitant such as an alkali.

It is usually preferred to add the alumina precursor compound in the form of alumina sol to the aforesaid mixture. If desired, however, the alumina precursor compound may be included in the mixture by performing the precipitate-forming reaction in step (a) in the presence of a water-soluble aluminum salt such as sodium aluminate, aluminum acetate or aluminum nitrate, thereby precipitating the water-insoluble alumina precursor compound together with the copper component.

When alumina sol is to be added to the mixed solid products from steps (a) and (b), the alumina sol may have an average particle diameter of 1 micron or less, preferably 0.2 micron or less, for good dispersibility.

The amount of the alumina precursor compound to be included in the mixed solid products can be varied depending upon the proportion of the aluminum compound required in the final catalyst. Generally, the amount is such that the Cu/Al atomic ratio is from 3/1 to 70/1, preferably from 5/1 to 65/1, more preferably from 7/1 to 50/1.

The mixture having the alumina precursor compound thus included therein is then calcined with or without prior treatment by kneading, drying, etc. The calcination may be performed by a method known per se. For example, the precipitate mixture is calcined by heating it at a temperature of at least 300° C., preferably at 330° to 400° C., usually for about 0.5 to 3 hours in an atmosphere of air, nitrogen, a combustible gas, etc. in a calcination furnace such as an electrical furnace or a gas calcination furnace. As a result, of this calcination, the copper component, the zinc component, the alumina precursor compound and the boron component are each converted to an oxide form.

The catalyst so obtained can be pulverized and molded by a tableting machine. Preferably, it is molded by pulverizing it, pre-molding the pulverized product by a molding machine, further pulverizing the pre-molded product, and then compression-molding it into tablets to afford a catalyst composition having mechanical strength high enough as a commercial catalyst.

The catalyst produced by the process of this invention described hereinabove is a Cu-Zn-Al three-component catalyst or a Cu-Zn-Al-B four-component catalyst. In the case of the Cu-Zn-Al three-component catalyst, the proportions of the copper, zinc and aluminum components are as follows on a metal atom percentage basis: copper, 30 to 70%, preferably 40 to 60%; zinc, 15 to 50%, preferably 20 to 40%; aluminum, 1 to 20%, preferably 4 to 16%. In the case of the Cu-Zn-Al-B four-component catalyst, the proportions of the copper, zinc, aluminum and boron components are as follows on an element atom percentage basis: copper, 30 to 70%, preferably 40 to 60%; zinc, 15 to 50%, preferably 20 to 40%; aluminum, 1 to 16%, preferably 3 to 12%; and boron, 0.1 to 5.0%, preferably 0.2 to 3.0%.

In the catalyst composition provided by the present invention, the copper, zinc, aluminum and boron elements are present usually in the form of oxide.

The catalyst composition of the present invention may contain a small amount of a metal atom in addition to the above components. For example, an alkali metal atom may be incorporated into it in an amount of 100 to 400 ppm.

The catalyst composition in accordance with this invention, after it is subjected to an activation treatment, for example by reduction with hydrogen as is usually practiced, can be used as a catalyst for various reactions, for example a reaction of synthesizing methanol from a gaseous mixture of carbon monoxide and/or carbon dioxide and hydrogen, a carbon monoxide conversion reaction, a hydrogenation reaction, and a methanol decomposition reaction.

The activation treatment of the catalyst composition in accordance with this invention may be performed in a customary manner. For example, it is carried out in a reducing atmosphere such as a starting gas for synthesis of methanol by raising the temperature of the catalyst composition gradually from about 140° C. to avoid abrupt generation of heat, and finally maintaining the catalyst composition at 240° C. for 3 hours.

The activated catalyst composition is particularly suitable as a reaction catalyst for synthesizing methanol from a gaseous mixture of carbon monoxide and/or carbon dioxide and hydrogen. Synthesis of methanol with the catalyst composition of this invention can be carried out by a method known per se, for example, by the method described in U.S. Pat. No. 3,971,735. For example, the synthetic reaction can be performed by feeding the aforesaid gaseous mixture to a reaction zone at a pressure of 20 to 300 atmospheres, preferably 30 to 150 atmospheres, a temperature of 150° to 300° C., preferably 200° to 280° C., and a space velocity of 2,000 to 50,000 $hr^{-1}$.

The catalyst composition provided by the process of this invention has various excellent advantages described below over conventional catalysts of the same type, and is very suitable for synthesis of methanol.

(a) It has high activity at relatively low temperatures and pressures.

(b) The cost of producing the catalyst is reduced. For example, by using zinc oxide and carbon dioxide gas, the cost of catalyst production decreases by 10 to 20% from that required in the case of precipitating zinc nitrate with alkali.

(c) The filtering operation during the manufacturing operation is easy, and the efficiency of catalyst preparation increases.

(d) It has a low abrasion rate and high compressive strength. In particular, the small difference between its abrasion rate before reduction and that after reduction is advantageous to its practical application.

(e) It has excellent moldability. One pre-molding cycle before its main molding step leads to catalyst strength sufficient for industrial application.

The following examples illustrate the present invention in greater detail.

EXAMPLE 1

Cupric nitrate trihydrate (195 kg) was dissolved in 1490 liters of deionized water, and the solution was maintained at about 30° C. Then, 134 kg of ammonium bicarbonate was dissolved in 1130 liters of deionized water, and the solution was maintained at about 30° C. With stirring, the aqueous solution of cupric nitrate prepared as above was added, and a precipitating reaction was performed with stirring. Thus, a copper slurry was prepared.

Separately, 49.4 kg of zinc oxide was put into 400 liters of deionized water, and the mixture was stirred for 30 minutes to prepare a slurry of zinc oxide. With stirring, the slurry of zinc oxide was added to the copper slurry, and then carbon dioxide gas was blown into the mixture. The temperature of the mixture at this time was maintained at about 30° C., and carbon dioxide gas was blown into it at a flow rate of 3.1 $Nm^3/hr$ for 2 hours. While continuing the blowing of carbon dioxide gas, the temperature of the solution was raised to 80° C., and the reaction was continued at this temperature for 30 minutes (that is, the blowing of carbon dioxide gas was continued for 2.5 hours from the beginning of the reaction) to age the reaction product.

The resulting copper-zinc slurry was filtered by a filter press. Filtration could be performed very easily within 10 minutes. The filter cake was washed with water, and 60 kg of alumina sol (10% aqueous solution of alumina) having an average particle diameter of 0.1 micron was added. They were kneaded for 30 minutes by a kneader. After the kneading, the mixture was dried at 100° C. for 17 hours, and then calcined in a calcination furnace at 370° C. for 2.5 hours. After the calcination, the resulting catalyst was pulverized to a size smaller than 14 mesh, and mixed with 3% of graphite. The mixture was molded, and a part of the molded product was used as a "primary product." The remaining molded product was again pulverized to a size of 14 mesh, and re-molded to form a "secondary product."

The resulting Cu-Zn-Al three-component catalyst had a Cu:Zn:Al atomic ratio of 54.4:42.2:3.4.

EXAMPLE 2

A catalyst was prepared in the same way as in Example 1 except that, after adding the zinc oxide slurry to the copper slurry, the temperature of the mixture was raised to 40° C., and carbon dioxide gas was blown into the mixture for 1 hour at a flow rate of 5.0 $Nm^3/hr$.

EXAMPLE 3

A catalyst was prepared in the same way as except that in Example 1, after adding the zinc oxide slurry to the copper slurry, the temperature of the mixture was raised to 55° C., and carbon dioxide gas was blown into the mixture at a flow rate of 8.0 $Nm^3/hr$ for 0.5 hour.

EXAMPLE 4

A catalyst was prepared in the same way as in Example 1 except that at the time of dissolving cupric nitrate in deionized water, 18.8 kg of boric acid was simultaneously dissolved in it. The resulting Cu-Zn-Al-B four-component catalyst had a Cu:Zn:Al:B atomic ratio of 54.3:42.1:3.4:0.2.

EXAMPLE 5

Cupric nitrate trihydrate (195 g) was dissolved in 1.5 liters of deionized water, and the solution was maintained at about 30° C. Then, 134 g of ammonium bicarbonate was dissolved in 1.1 liters of deionized water, and the solution was maintained at about 30° C. With stirring, the aqueous solution of cupric nitrate was added, and a precipitating reaction was preformed with stirring. Thus, a copper slurry was prepared.

Separately, 60.3 g of zinc hydroxide was put into 0.4 liter of deionized water, and the mixture was stirred for 30 minutes to prepare a slurry of zinc hydroxide. The zinc hydroxide slurry was added to the above copper slurry, and carbon dioxide gas was blown into the mixture. At this time, the mixture was maintained at about 30° C., and carbon dioxide gas was blown into it at a flow rate of 3 N liter/hr for 2 hours. While continuing blowing of carbon dioxide gas, the temperature of the solution was raised to 80° C., and the reaction was continued for 30 minutes at this temperature to age it. Blowing of carbon dioxide gas was effected for 2.5 hours from the beginning of the reaction, and was stopped.

The resulting copper-zinc slurry was filtered by a filter press. The filter cake was washed with water, and 60 g of alumina sol (10% aqueous solution of alumina) having an average particle diameter of 0.1 micron was added. They were kneaded by a kneader for 30 minutes, and the kneaded mixture was worked up in the same way as in Example 1 to prepare a catalyst.

The resulting catalyst had a Cu:Zn:Al atomic ratio of 54.6:42.1:3.3.

COMPARATIVE EXAMPLE 1

An aqueous solution of cupric nitrate was prepared by dissolving 130 kg of cupric nitrate trihydrate in 946 liters of deionized water, and the solution was maintained at about 30° C. An aqueous solution of zinc nitrate was prepared by dissolving 120 kg of zinc nitrate hexahydrate in 686 liters of deionized water, and the solution was maintained at about 30° C.

Separately, a solution of 93.6 kg of ammonium bicarbonate in 1089 liters of deionized water was put into a 6000-liter reaction vessel, and maintained at about 30° C. While this solution was stirred, the aqueous solution of cupric nitrate trihydrate was added, and the mixture was reacted at 30° C. for 15 minutes to form a slurry. To the slurry was added, with stirring, an aqueous solution, kept at 30° C., of 32.3 kg of sodium hydroxide in 775 liters of deionized water. The aqueous solution of zinc nitratre was further added, and with continued stirring, the reaction was performed for 10 minutes. Then the solution in the reaction vessel was heated to 80° C., and maintained at this temperature for 30 minutes with stirring to age it. The aged mixture was then allowed to cool.

The resulting slurry was filtered in the same manner as in Example 1. The filtration required a period of 50 minutes despite the fact that the amount of the product formed was adjusted to 70% of that in Example 1.

The filter cake was washed with water, and then kneaded with 40 kg of alumina sol having an average particle diameter of 0.1 micron for 40 minutes in a kneader. Subsequently, the kneaded mixture was subjected to the steps of drying, calcination, pulverization, graphite addition, molding, pulverization and re-molding in the same way as in Example 1.

The resulting catalyst had a Cu:Zn:Al atomic ratio of 55:41:4.

COMPARATIVE EXAMPLE 2

Cupric nitrate trihydrate (130 kg), 120 kg of zinc nitrate hexahydrate and 12.5 kg of boric acid were dissolved in 1670 liters of deionized water, and maintained at 80° C. A solution of 120 kg of sodium carbonate in 1440 liters of deionized water, kept at 80° C., was added to the resulting solution to co-precipitate copper and zinc, and the slurry was continuously stirred at this temperature for 30 minutes to age it. The aged slurry was then allowed to cool.

The resulting slurry was filtered and washed with water in the same way as in Example 1. To the filter cake was added 40 kg of alumina sol (10% aqueous solution of alumina) having an average particle diameter of 0.1 micron, and they were kneaded for 40 minutes by a kneader. The kneaded mixture was then subjected to the steps of drying, calcination, pulverization, graphite addition, molding, pulverization and re-molding in the same way as in Example 1 to form a catalyst.

The resulting Cu-Zn-Al-B four-component catalyst had a Cu:Zn:Al:B atomic ratio of 54.9:41.1:3.8:0.2.

REFERENCE EXAMPLE 1

Each of the catalysts prepared in Examples 1 to 6 and Comparative Examples 1 and 2 above was pulverized to a size of 20 to 40 mesh, and maintained at 140° C. in a nitrogen gas stream. It was heated while slowly adding a synthesis gas to avoid violent heat generation, and finally maintained at 240° C. for 3 hours to reduce it.

Then, a methanol-synthesizing reaction was performed at a pressure of 70 kg/cm$^2$.G, a space velocity of $2 \times 10^4$ hr$^{-1}$ and a reaction temperature of 260° C. by using the resulting catalyst and a methanol decomposition gas consisting of 70% $H_2$, 23% CO, 3% $CO_2$, 3.5% $CH_4$ and 0.5% $N_2$. To determine the life of the catalyst within a short period of time, the activity of the catalyst was measured when the synthesis of methanol was performed for 2 hours with the temperature of the catalyst raised to 360° C. and then the temperature was lowered to 260° C.; when the treatment was further performed for 4 hours at 360° C. (total time 6 hours); and when the treatment was further conducted for 4 hours (total time 10 hours) with the temperature raised to 360° C. and then the temperature was lowered again to 260° C. The results are shown in Table 1 in terms of the concentration of methanol in the outlet gas.

TABLE 1

| Catalyst | | Methanol concentration in outlet gas (mol %) | | | |
|---|---|---|---|---|---|
| | | Initial Period | 360° C., 2 hr | 360° C., 6 hr | 360° C., 10 hr |
| Ex. 1 | Primary | 14.1 | 13.3 | 12.9 | 12.6 |
| | Secondary | 14.1 | 13.4 | 13.0 | 12.6 |
| Ex. 2 | Primary | 13.7 | 13.0 | 12.4 | 11.9 |
| | Secondary | 13.7 | 13.0 | 12.4 | 11.9 |
| Ex. 3 | Primary | 13.5 | 12.7 | 12.2 | 11.7 |

TABLE 1-continued

| | | Methanol concentration in outlet gas (mol %) | | | |
|---|---|---|---|---|---|
| Catalyst | | Initial Period | 360° C., 2 hr | 360° C., 6 hr | 360° C., 10 hr |
| | Secondary | 13.5 | 12.7 | 12.3 | 11.8 |
| CEx. 1 | Primary | 14.1 | 13.0 | 12.5 | 12.1 |
| | Secondary | 14.2 | 13.1 | 12.6 | 12.1 |
| CEx. 2 | Primary | 12.6 | 11.8 | 11.4 | 11.2 |
| | Secondary | 12.6 | 11.8 | 11.4 | 11.2 |

*Ex. = Example; CEx. = Comparative Example

REFERENCE EXAMPLE 2

A cylindrical drum (100 mm in diameter) having a JIS 6-mesh wire gauze applied to the circumferential surface was charged with 10 g of each of the catalysts in tablet form obtained in Examples 1 to 5 and Comparative Examples 1 and 2 (before and after reduction under the conditions described in Reference Example 1). The drum was rolled at 160 rpm for 20 minutes. The abrasion rate was calculated from the following equation.

$$\text{Abrasion rate (\%)} = \frac{\text{Amount (g) of sample taken} - \text{Amount (g) of sample remaining in drum}}{\text{Amount (g) of sample taken}} \times 100$$

The results are shown in Table 2.

TABLE 2

| | Abrasion rate (%) | | | |
|---|---|---|---|---|
| | Primary product | | Secondary product | |
| Catalyst | Before reduction | After reduction | Before reduction | After reduction |
| Example 1 | 5.9 | 8.1 | 4.3 | 2.1 |
| Example 2 | 5.5 | 8.0 | 4.3 | 2.0 |
| Example 3 | 4.7 | 7.8 | 4.6 | 2.4 |
| Example 4 | 4.2 | 8.0 | 3.4 | 1.0 |
| Example 5 | 5.8 | 8.3 | 4.3 | 2.0 |
| Comparative Example 1 | 6.3 | 51.7 | 3.4 | 1.4 |
| Comparative Example 2 | 7.0 | 88.2 | 6.1 | 76.8 |

When the catalyst of Comparative Example 2 was again pulverized and molded, the abrasion rates became much the same as in Examples 1 to 5.

REFERENCE EXAMPLE 3

The compressive strength in the longitudinal direction (the direction of the central axis) each of the catalysts in pellet form obtained in Examples 1 to 5 and Comparative Examples 1 and 2 (before reduction and after reduction under the conditions described in Reference Example 1) was measured by a small-sized material testing machine (a product of Fujii Seiki Co., Ltd.; model PSP-300). The results are shown in Table 3.

TABLE 3

| | Compressive strength (kg/cm$^2$) | | | |
|---|---|---|---|---|
| | Primary product | | Secondary product | |
| Catalyst | Before reduction | After reduction | Before reduction | After reduction |
| Example 1 | 255 | 251 | 252 | 231 |
| Example 2 | 248 | 240 | 267 | 239 |
| Example 3 | 281 | 275 | 253 | 231 |
| Example 4 | 253 | 250 | 274 | 253 |
| Example 5 | 270 | 261 | 269 | 246 |
| Comparative Example 1 | 266 | 263 | 257 | 220 |
| Comparative Example 2 | 271 | 272 | 278 | 235 |

What we claim is:

1. A process for preparing a catalyst composition comprising copper oxide, zinc oxide and aluminum oxide as essential ingredients which comprises,
    (a) a step of precipitating, from an aqueous solution of water-soluble copper salt, the copper component, using an alkaline substance selected from alkali carbonates and alkali bicarbonates as a precipitant;
    (b) a step of blowing carbon dioxide gas into an aqueous dispersion of a zinc compound selected from zinc oxide and zinc hydroxide to convert the zinc compound to basic zinc carbonate; and
    (c) a step of calcining a mixture of the solid products obtained in steps (a) and (b) in the presence of an alumina precursor compound.

2. A process for preparing a catalyst composition as defined in claim 1 'with the additional component boron oxide.'

3. The process of claim 1 wherein the water-soluble copper salt is cupric nitrate.

4. The process of claim 1 wherein the aqueous solution of the water-soluble copper salt contains the copper salt in a concentration of 0.1 to 2.0 mole/liter.

5. The process of claim 1 or 2 wherein the alkaline substance is selected from the group consisting of sodium carbonate, potassium carbonate, lithium carbonate, ammonium carbonate, sodium bicarbonate, potassium bicarbonate and ammonium bicarbonate.

6. The process of claim 1 or 2 wherein the alkaline substance is used in a proportion of at least 0.8 equivalent per equivalent of the copper salt to be precipitated.

7. The process of claim 1 or 2 wherein step (a) is carried out at a temperature ranging from ambient temperature to about 60° C.

8. The process of claim 1 or 2 wherein the aqueous dispersion of the zinc compound contains the zinc compound in a concentration of 5 to 30% by weight.

9. The process of claim 1 or 2 wherein the carbon dioxide gas is used in a proportion of at least 0.3 mole per mole of the zinc compound.

10. The process of claim 1 or 2 wherein step (b) is carried out at a temperature ranging from ambient temperature to about 100° C.

11. The process of claim 1 or 2 wherein after step (a) and/or step (b), the resulting slurry is aged for at least 5 minutes at a temperature of about 60° C. to about 100° C.

12. The process of claim 2 wherein the water-soluble boron compound is boric acid or borax.

13. The process of claim 2 wherein the water-soluble boron compound is used at a B/Zn atomic ratio of from 0.1 to 1.5 with respect to the zinc compound used in step (b).

14. The process of claim 1 or 2 wherein the alumina precursor compound is an alumina sol, or aluminum hydroxide obtained by precipitation from an aqueous solution of a water-soluble aluminum compound.

15. The process of claim 1 or 2 wherein the alumina sol has an average particle diameter of at most 1 micron.

16. The process of claim 1 or 2 wherein the amount of the alumina precursor compound is such that the Cu/Al atomic ratio is in the range of from 3/1 to 70/1.

17. The process of claim 1 or 2 wherein the calcination is performed at a temperature of at least 300° C.

* * * * *